United States Patent [19]

Pawloski

[11] 4,375,546
[45] Mar. 1, 1983

[54] SUBSTITUTED PYRIDINYL ESTERS OF 2-(1-OXOALKYLOXY)ETHYL CARBAMIC ACID

[75] Inventor: Chester E. Pawloski, Bay City, Mich.

[73] Assignee: The Dow Chemical Company, Midland, Mich.

[21] Appl. No.: 321,354

[22] Filed: Nov. 16, 1981

[51] Int. Cl.³ .......................................... C07D 213/64
[52] U.S. Cl. .................... 546/292; 546/288; 546/291; 424/263; 71/94
[58] Field of Search .................. 546/288, 292, 291

[56] References Cited

U.S. PATENT DOCUMENTS

| 3,249,619 | 5/1966 | Johnston | 546/292 |
| 3,409,624 | 11/1968 | De Selms | 546/292 |
| 3,630,714 | 12/1971 | De Selms | 71/94 |
| 3,701,779 | 10/1972 | Donninger et al. | 546/292 |
| 4,180,395 | 12/1979 | Johnston et al. | 71/94 |
| 4,278,809 | 7/1981 | Burdett | 560/222 |

Primary Examiner—Alan L. Rotman

[57] ABSTRACT

Substituted pyridinols are reacted with an isocyanatoethyl alkanoate in an inert solvent in the presence of an activating agent to form a group of biologically active organic compounds. These compounds are useful as broad spectrum herbicides effective against a variety of grassy weeds, broadleaf weeds and grassy crops. Compounds of this invention may also be utilized as fungicides.

4 Claims, No Drawings

SUBSTITUTED PYRIDINYL ESTERS OF 2-(1-OXOALKYLOXY)ETHYL CARBAMIC ACID

BACKGROUND OF THE INVENTION

The present invention discloses novel, biologically active organic compounds and their method of preparation. These compounds may be utilized as herbicides and fungicides.

SUMMARY OF THE INVENTION

The present invention is directed to a group of novel, biologically active compounds. These compounds are represented by the formula:

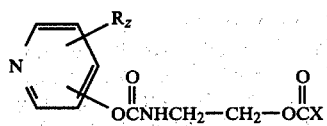

wherein R may independently be hydrogen, halo, alkyl, nitro, alkyloxy, cyano, alkylthio or phenyl; X is alkyl; and z is an integer of from 1 to 4, both inclusive.

As used herein, the term "alkyl" refers to aliphatic, straight or branched chain radicals of from about one to about four carbon atoms inclusive; the term "halo" refers to atoms selected from the group consisting of chlorine, bromine, fluorine and the like.

The compounds of the present invention are biologically active and useful as herbicides and fungicides. Typically, these compounds are effective against grasses and plants such as pigweed, crabgrass, morning glory, yellow foxtail and barnyard grass. As fungicides, these compounds are typically effective against the causative organisms of diseases such as barley powdery mildew.

The compounds of this invention may be prepared by the reaction of a suitably substituted pyridinol with an isocyanatoethyl alkanoate. The preparation of the pyridinols used as starting material for this invention is well known in the art, and may be readily prepared by utilizing known procedures. Similarly, the preparation of the isocyanatoethyl alkanoate may be carried out by known processes such as the reaction of 2-alkyl oxazoline with phosgene in a two-phase system of methylene chloride and aqueous caustic.

In the preparation of the compounds of this invention, the reactants are contacted with one another in an inert solvent such as acetone or methyl ethyl ketone in the presence of a small amount of activating agent which may be, for example, triethylamine or dibutyltin dilaurate. While the exact proportion of the reactants employed is not critical, the reaction consumes the reactants in amounts representing essentially equimolar proportions and the use of equimolar amounts is preferred. The mixture is then stirred at reflux temperature for a period of time sufficient to assure substantial completion of the reaction and to obtain the desired substituted pyridinyl ester of 2-(1-oxoalkyloxy)ethyl carbamic acid. Following reaction, the solvent is removed by conventional techniques and the residue containing the desired product is recrystallized from a suitable solvent such as n-hexane.

DESCRIPTION OF SOME PREFERRED EMBODIMENTS

The following examples are included to further demonstrate the invention, and are not intended as a limitation thereon.

EXAMPLE 1:

2,3,5,6-Tetrachloro-4-pyridinyl ester of (2-(1-oxopropoxy)ethyl)carbamic acid 11.7 Grams of 2,3,5,6-tetrachloro-4-pyridinol, 7.2 grams of isocyanatoethyl propionate, and a few drops of dibutyltin dilaurate (as activating agent) were added to 200 ml of acetone and stirred at reflux temperature for eight hours and then allowed to stand. The mixture was again stirred at reflux temperature for an additional seven hours before the addition of 6.0 grams of potassium carbonate. The reactants were then stirred for another hour after which the insoluble components were filtered off and the solvent removed under reduced pressure, leaving a residue. The resulting residue was slurried in n-hexane, cooled, and filtered to yield about 15 grams of soft, white solid as the desired 2,3,5,6-tetrachloro-4-pyridinyl ester of (2-(1-oxopropoxy)ethyl)carbamic acid.

EXAMPLE 2:

2,3,5-Trichloro-4-pyridinyl ester of (2-(1-oxopropoxy)ethyl)carbamic acid

Following substantially the same procedure as outlined in Example 1, 9.9 grams of 2,3,5-trichloro-4-pyridinol, 7.8 grams of isocyanatoethyl propionate and a few drops of dibutyltin dilaurate were combined. Approximately 16.5 grams of the desired compound, the 2,3,5-trichloro-4-pyridinyl ester of (2-(1-oxopropoxy)-ethyl)carbamic acid was recovered having a melting point of 222° C. (decomposition).

EXAMPLE 3:

2,3,5,6-Tetrachloro-4-pyridinyl ester of (2-(acetoxy)ethyl)carbamic acid 11.7 Grams of 2,3,5,6-tetrachloro-4-pyridinol, 6.5 grams of isocyanatoethyl acetate and a few drops of dibutyltin dilaurate were stirred in 200 ml of acetone at 40° C. for eight hours, and subsequently stirred at room temperature for an additional 20 hours. The solvent was removed under reduced pressure, and the remaining oily residue was slurried in 300 ml of n-hexane. The resulting insoluble solids were filtered off and dried leaving about 13 grams of the desired product. The n-hexane phase was distilled under reduced pressure and approximately 4 grams of additional product, the 2,3,5,6-tetrachloro-4-pyridinyl ester of (2-(acetoxy)ethyl)carbamic acid was obtained having a melting point of 78°–80° C.

EXAMPLE 4:

3,5,6-Trichloro-2-pyridinyl ester of (2-(acetoxy)ethyl)carbamic acid 9.0 Grams of 3,5,6-trichloro-2-pyridinol, 5.8 grams of isocyanatoethyl acetate and a few drops of dibutyltin dilaurate were mixed together in 200 ml of methyl ethyl ketone and stirred at 60° C. for five hours and allowed to stand. The mixture was then stirred for an additional three hours at 60° C. after which, the solvent was removed under reduced pressure. The resulting solids were slurried in about 200 ml of n-hexane, filtered and dried leaving about 13.2 grams of the desired product, the 3,5,6-trichloro-2-pyridinyl ester of (2-(acetoxy)ethyl)carbamic acid, melting at 83°–85° C.

The compounds of the present invention may be used as fungicides, herbicides, or both. For these uses, one or more of the compounds may be used in unmodified form, or may be formulated into herbicidal or fungicidal compositions. For instance, compounds of this invention may be employed as a dispersion in a finely divided solid and applied as a dust. The compounds may also be formulated into aqueous compositions with or without the use of a wetting agent and applied as a spray. Similarly, the compounds may be employed in liquid organic compositions, water-in-oil or oil-in-water emulsions or aqueous dispersions with or without the use of emulsifying, wetting or dispersing agents.

Not all compounds or the compositions containing them may be equally effective at similar concentrations or against similar plant or fungal organisms. While the exact amount of compound or composition employed is not critical, good results are obtained when the plant, organism, and/or their habitat is contacted with a herbicidally or fungicidally effective amount of one or more of the compounds or compositions containing them. The term "effective amount" refers to a herbicidal or fungicidal concentration of from about 62.5 to about 2000 parts per million (ppm).

In a representative operation, the post-emergence activity of the compounds of the present invention was demonstrated. Various plant species representing grassy weeds, broadleaf weeds and grassy crops were grown in four separate plots so that each plot contained all of the species. The plants in each plot were grown to a height of about four inches, and then each plot was sprayed to run-off with one of four aqueous compositions of test compound prepared in concentrations of 500, 250, 125, and 62.5 ppm by weight. The plants were placed in an environment conducive to growth and were evaluated two weeks later. The results of the test are summarized in Table I where the results are expressed in terms of percent kill of the particular plant species.

TABLE I

| Example No. | Concentration (ppm) | Sugar Beets | Pigweed | Sorghum | Crabgrass |
|---|---|---|---|---|---|
| 1 | 500 | 100 | 100 | 30 | 100 |
|   | 250 | 100 | 100 | 40 | 100 |
|   | 125 | 100 | 70 | 20 | 100 |
|   | 62.5 | 0 | 30 | 0 | 100 |
| 2 | 500 | 100 | 100 | 80 | 100 |
|   | 250 | 0 | 100 | 80 | 100 |
|   | 125 | NT* | 70 | 50 | 100 |
|   | 62.5 | NT* | 50 | 40 | 20 |
| 3 | 500 | 90 | 100 | 50 | 100 |
|   | 250 | 100 | 100 | 60 | 100 |
|   | 125 | 95 | 100 | 30 | 100 |
|   | 62.5 | 50 | 100 | 0 | 100 |

*NT = Not Tested

In another operation, the fungicidal activity of compounds of this invention was demonstrated when soil and foliar applications of 500 ppm of one of the compounds was applied to the test plants. The compounds of Examples 1, 2 and 3 each showed 90, 100 and 93 percent control respectively of the causative organism of barley powdery mildew.

What is claimed is:

1. A compound corresponding to the formula:

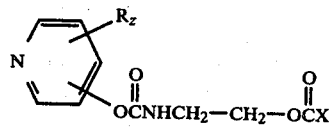

wherein R is hydrogen or halo; X is alkyl of one to four carbon atoms; and z is an integer of from 1 to 4, both inclusive.

2. The compound of claim 1 which is the 2,3,5,6-tetrachloro-4-pyridinyl ester of (2-(1-oxopropoxy)ethyl)carbamic acid.

3. The compound of claim 1 which is the 2,3,5,-trichloro-4-pyridinyl ester of (2-(1-oxopropoxy)-ethyl)-carbamic acid.

4. The compound of claim 1 which is the 2,3,5,6-tetrachloro-4-pyridinyl ester of (2-(acetoxy)-ethyl)carbamic acid.

* * * * *